(12) United States Patent
Joseph et al.

(10) Patent No.: US 12,599,722 B2
(45) Date of Patent: Apr. 14, 2026

(54) SYRINGE HOLDER

(71) Applicant: SHL MEDICAL AG, Zug (CH)

(72) Inventors: Abhilash Joseph, Gustavsberg (SE);
John Wiklund, Stockholm (SE)

(73) Assignee: SHL Medical AG, Zug (CH)

( * ) Notice: Subject to any disclaimer, the term of this
patent is extended or adjusted under 35
U.S.C. 154(b) by 755 days.

(21) Appl. No.: 17/911,013

(22) PCT Filed: Mar. 31, 2021

(86) PCT No.: PCT/EP2021/058535
§ 371 (c)(1),
(2) Date: Sep. 12, 2022

(87) PCT Pub. No.: WO2021/213790
PCT Pub. Date: Oct. 28, 2021

(65) Prior Publication Data
US 2023/0089027 A1      Mar. 23, 2023

(30) Foreign Application Priority Data
Apr. 21, 2020    (EP) ..................................... 20170705

(51) Int. Cl.
A61M 5/24 (2006.01)
A61M 5/20 (2006.01)

(52) U.S. Cl.
CPC ............... A61M 5/24 (2013.01); A61M 5/20
(2013.01); *A61M 2005/2006* (2013.01);
(Continued)

(58) Field of Classification Search
CPC ........ A61M 5/24; A61M 5/20; A61M 5/2403;
A61M 5/244; A61M 5/2407; A61M
5/2006
See application file for complete search history.

(56) References Cited

U.S. PATENT DOCUMENTS

| | | | |
|---|---|---|---|
| 4,927,416 A | 5/1990 | Tomkiel | |
| 7,815,598 B2 | 10/2010 | Hommann et al. | |

(Continued)

FOREIGN PATENT DOCUMENTS

| | | | |
|---|---|---|---|
| CN | 108136125 A | 6/2018 | |
| CN | 109922848 A | 6/2019 | |

(Continued)

OTHER PUBLICATIONS

International Search Report and Written Opinion for Int. App. No.
PCT/EP2021/058535, mailed Apr. 30, 2021.

*Primary Examiner* — Tasnim Mehjabin Ahmed
(74) *Attorney, Agent, or Firm* — McDonnell Boehnen
Hulbert & Berghoff LLP

(57) ABSTRACT

A syringe holder for an autoinjector is presented having a
tubular body extending around an axis in a circumferential
direction and along the axis in an axial direction, the tubular
body having a cut-out extending from a distal end of the
tubular body and a flexible expansion joint extending across
the cut-out in the circumferential direction. The tubular body
can also have an inner surface and an outer surface, a first
cut-out in the tubular body, the first cut-out extending in an
axial direction from a proximal end of the tubular body and
either a recess in the inner surface of the tubular body, the
recess extending in the axial direction from the distal end of
the tubular body, or a second cut-out in the tubular body, the
second cut-out extending in the axial direction from a distal
end of the tubular body.

13 Claims, 10 Drawing Sheets

(52) U.S. Cl.
CPC .............. *A61M 2005/2403* (2013.01); *A61M 2005/2407* (2013.01); *A61M 2005/244* (2013.01)

(56) References Cited

U.S. PATENT DOCUMENTS

| | | | |
|---|---|---|---|
| 8,647,299 B2 | 2/2014 | Stamp | |
| 9,713,678 B2 | 7/2017 | Hourmand et al. | |
| 2009/0308895 A1 | 12/2009 | Reynolds et al. | |
| 2019/0060579 A1 | 2/2019 | Daniel | |
| 2019/0081578 A1 | 3/2019 | Seneviratne et al. | |
| 2019/0307967 A1 | 10/2019 | Holmqvist | |
| 2020/0188605 A1* | 6/2020 | Boström | A61M 5/326 |

FOREIGN PATENT DOCUMENTS

| | | | |
|---|---|---|---|
| EP | 2252350 B1 | 4/2016 | |
| EP | 2788055 B1 | 2/2017 | |
| EP | 3323448 A1 | 5/2018 | |
| EP | 2788052 B1 | 4/2019 | |
| JP | 2001513656 A | 9/2001 | |
| JP | 2003225308 A | 8/2003 | |
| JP | 2015500125 A | 10/2017 | |
| WO | 2011/123024 A1 | 10/2011 | |
| WO | 2012/135524 A1 | 10/2012 | |
| WO | 2013/089620 A1 | 6/2013 | |
| WO | 2017/071909 A1 | 5/2017 | |
| WO | 2017/114906 A1 | 7/2017 | |
| WO | 2017/143461 A1 | 8/2017 | |
| WO | 2018/015119 A1 | 1/2018 | |
| WO | 2019/081578 A1 | 5/2019 | |
| WO | 2019/185335 A1 | 10/2019 | |
| WO | 2019/197493 A1 | 10/2019 | |
| WO | 2019224782 A1 | 11/2019 | |

* cited by examiner

SYRINGE HOLDER

CROSS REFERENCE TO RELATED APPLICATIONS

The present application is a U.S. National Phase Application pursuant to 35 U.S.C. § 371 of International Application No. PCT/EP2021/058535 filed Mar. 31, 2021, which claims priority to European Patent Application No. 20170705.6 filed Apr. 21, 2020. The entire disclosure contents of these applications are herewith incorporated by reference into the present application.

TECHNICAL FIELD

The present disclosure concerns syringe holders for medicament delivery devices such as autoinjectors, and particularly to syringe holders comprising a recess, a cut-out or an expansion joint.

BACKGROUND

Medicament delivery devices such as autoinjectors often include a syringe holder to support the syringe within the autoinjector; see WO 2013/089620 for an example of a syringe holder. Such syringe holders work well, but it can be difficult to insert the syringe into the syringe holder, and there can be a risk of damaging the syringe holder during insertion of the syringe into the syringe holder, particularly for syringes that include bypasses. The applicant has appreciated that improvements could be made to the syringe holder to alleviate this issue.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "radial" and "radially" refer to a direction extending from the axis and generally perpendicular to the longitudinal direction.

A first aspect of the present disclosure comprises a syringe holder for an autoinjector, the syringe holder comprising a tubular body extending around an axis in a circumferential direction and along the axis in an axial direction from a proximal end to a distal end, the tubular body comprising a cut-out extending from the distal end of the tubular body and a flexible expansion joint extending across the cut-out in the circumferential direction. Preferably, the expansion joint is configured to flex in the circumferential direction. The syringe holder can help alleviate stress on the syringe holder during and after insertion of a syringe into the syringe holder, particularly when the syringe has a bypass. It can also help reduce part breakage during and after assembly. Increasing flexibility of the syringe holder, for example by including an expansion joint, can also reduce the forces on the tools used for assembly, which can result in tools lasting longer.

Preferably, the tubular body comprises an inner surface and an outer surface, and the tubular body comprises a recess in the inner surface. Providing a recess can reduce or avoid the need for the syringe holder to deform during insertion of a syringe.

Preferably, the tubular body comprises a window, the window extending in the axial direction and spaced apart from the distal end of the tubular body and from the proximal end of the tubular body. Preferably, the tubular body comprises two windows, each window extending in the axial direction and spaced apart from the distal end of the tubular body and from the proximal end of the tubular body. Provision of a window or windows can reduce stress on the syringe, for example by making it easier for the syringe holder to flex during insertion of the syringe and/or by providing space for a syringe bypass to extend after the syringe is inserted without tensioning the syringe holder. Preferably, when two windows are provided, the windows are opposite each other relative to the axis. Provision of a window can alternatively or additionally allow the drug in the syringe to be visible after assembly of an autoinjector. Preferably, the window extends further in the axial direction than in the circumferential direction.

Preferably, the tubular body comprises a proximal end cut-out extending from the proximal end of the tubular body. This can also help increase flexibility of the syringe holder and reduce stress on the syringe holder and the syringe, and can also help support the syringe.

Preferably, a first of the two windows extends from the proximal end of the cut-out, and wherein a second of the two windows extends from the distal end of the cut-out. Preferably, the recess extends from the distal end of the tubular body. Preferably, the recess is deeper at the proximal end of the recess than at the distal end of the recess. Preferably, a portion of the inner surface in the recess is angled relative to the axis. These recess features can stop the syringe from falling back out of the syringe holder. Alternatively, the recess is deeper at the distal end of the recess than at the proximal end of the recess. This can make it easier to insert the syringe into the syringe holder (e.g. FIG. 8).

Preferably, the tubular body comprises a second cut-out extending from the distal end of the tubular body, wherein the second cut-out is spaced apart from the cut-out in the circumferential direction, and wherein the proximal end of the second cut-out is adjacent to the distal end of the recess. This can further help increase syringe holder flexibility and reduce stress on the syringe holder. It can also make inserting the syringe into the syringe holder easier. Preferably, the expansion joint is closer to the distal end of the tubular body than to the proximal end of the tubular body.

A second aspect of the present disclosure comprises a syringe holder comprising a tubular body extending around an axis in a circumferential direction and along the axis in an axial direction from a proximal end to a distal end, wherein the tubular body comprises an inner surface and an outer surface, a first cut-out in the tubular body, the first cut-out extending in the axial direction from the proximal end of the tubular body; and either a recess in the inner surface of the tubular body, the recess extending in the axial direction from the distal end of the tubular body, or a second cut-out in the tubular body, the second cut-out extending in the axial direction from the distal end of the tubular body. As with the first aspect of the present disclosure, this design can help alleviate stress on the syringe holder during and after insertion of a syringe into the syringe holder, particularly when the syringe has a bypass. It can also help reduce part breakage during and after assembly. Increasing flexibility of the syringe holder, for example by including an expansion joint, can also reduce the forces on the tools used for assembly, which can result in tools lasting longer.

Preferably, the tubular body comprises a second cut-out in the tubular body, the second cut-out extending in the axial direction from the distal end of the tubular body, and wherein the tubular body comprises a recess that extends from the proximal end of the second cut-out. This can further help increase syringe holder flexibility and reduce stress on the syringe holder. It can also make inserting the syringe into the syringe holder easier.

Preferably, the recess is deeper in the direction perpendicular to the axis at the distal end of the recess than at the proximal end of the recess. This can stop the syringe from falling back out of the syringe holder.

Preferably, a recess of the first aspect or the second aspect is configured to receive a part of a syringe when said syringe is inserted into the syringe holder during assembly of a medicament delivery device. Preferably, the part of said syringe is a bypass of said syringe.

A third aspect of the present disclosure comprises an autoinjector comprising a syringe holder as described above. Preferably, the autoinjector comprises a syringe inside the syringe holder. Preferably, the syringe comprises a bypass. Preferably, the bypass extends in a cut-out, a recess or a window of the syringe holder.

A fourth aspect of the present disclosure comprises a syringe holder for an autoinjector, the syringe holder comprising a tubular body extending around an axis in a circumferential direction and along the axis in an axial direction from a proximal end to a distal end, the tubular body comprising an inner surface and an outer surface, a window in the tubular body, the window extending in the axial direction and spaced apart from the distal end of the tubular body and from the proximal end of the tubular body, and the tubular body comprising at least one of:

a recess in the inner surface, the recess extending from the distal end of the tubular body;

a cut-out extending from the distal end of the tubular body; and an expansion joint configured to flex in the circumferential direction.

Preferably, the tubular body comprises the recess in the inner surface, and wherein the recess is deeper at the proximal end of the recess than at the distal end of the recess. Preferably, the tubular body comprises the cut-out extending from the distal end, and the tubular body comprises a recess extending in the axial direction from the proximal end of the cut-out. Preferably, the tubular body comprises a second cut-out extending from the proximal end of the tubular body.

A fifth aspect of the present disclosure comprises a syringe holder for receiving a syringe of an autoinjector, the syringe holder comprising a tubular body with an outer surface and an inner surface, wherein the inner surface comprises a recess or a cut-out configured to receive a bypass portion of a syringe, and wherein the syringe holder comprises a C-clip at the proximal end.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

BRIEF DESCRIPTION OF THE DRAWINGS

Embodiments of the present disclosure will now be described by way of example only and with reference to the accompanying drawings, in which.

DETAILED DESCRIPTION

Figure 1:
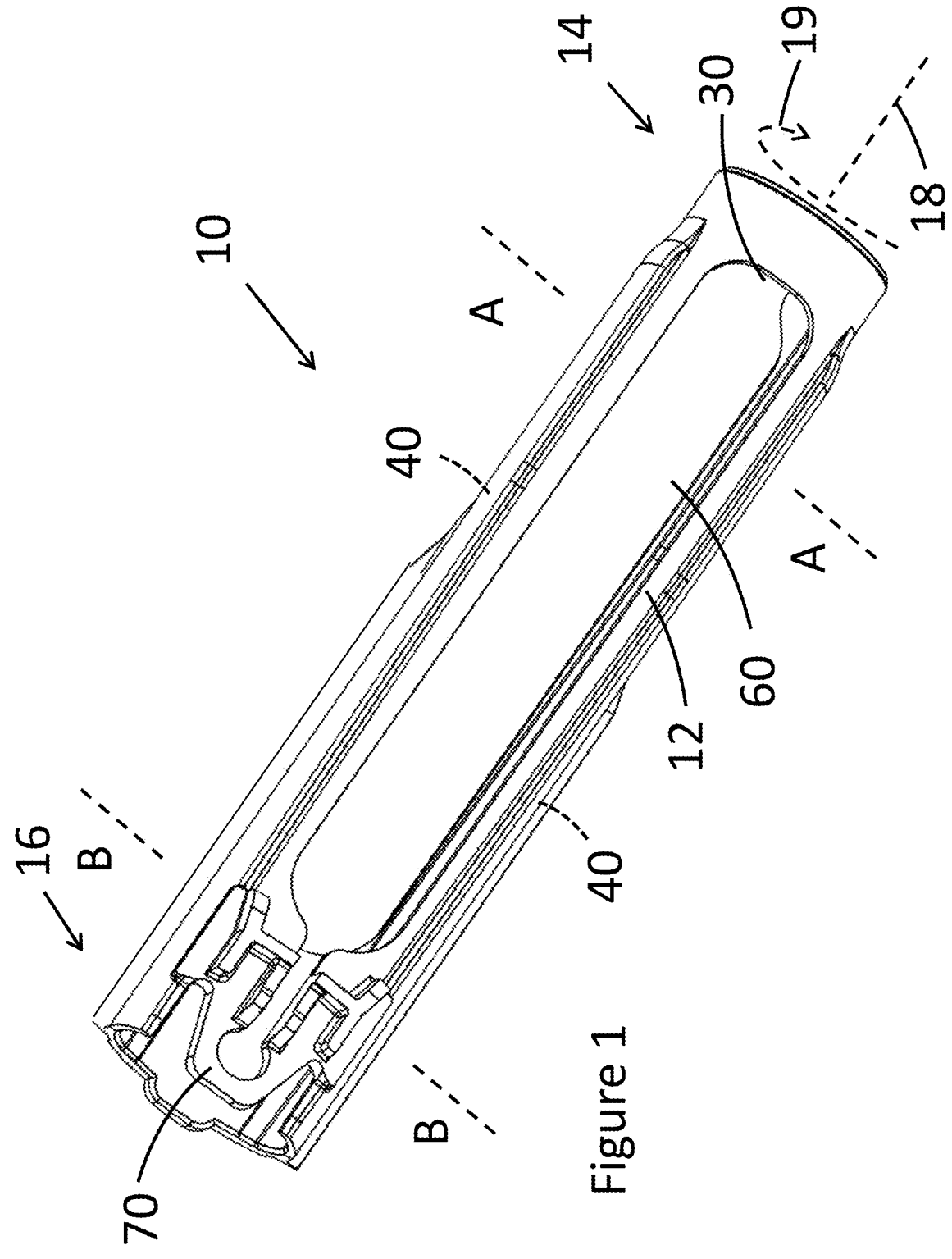
FIG. 1 shows a perspective view of an example syringe holder.
Figure 2:
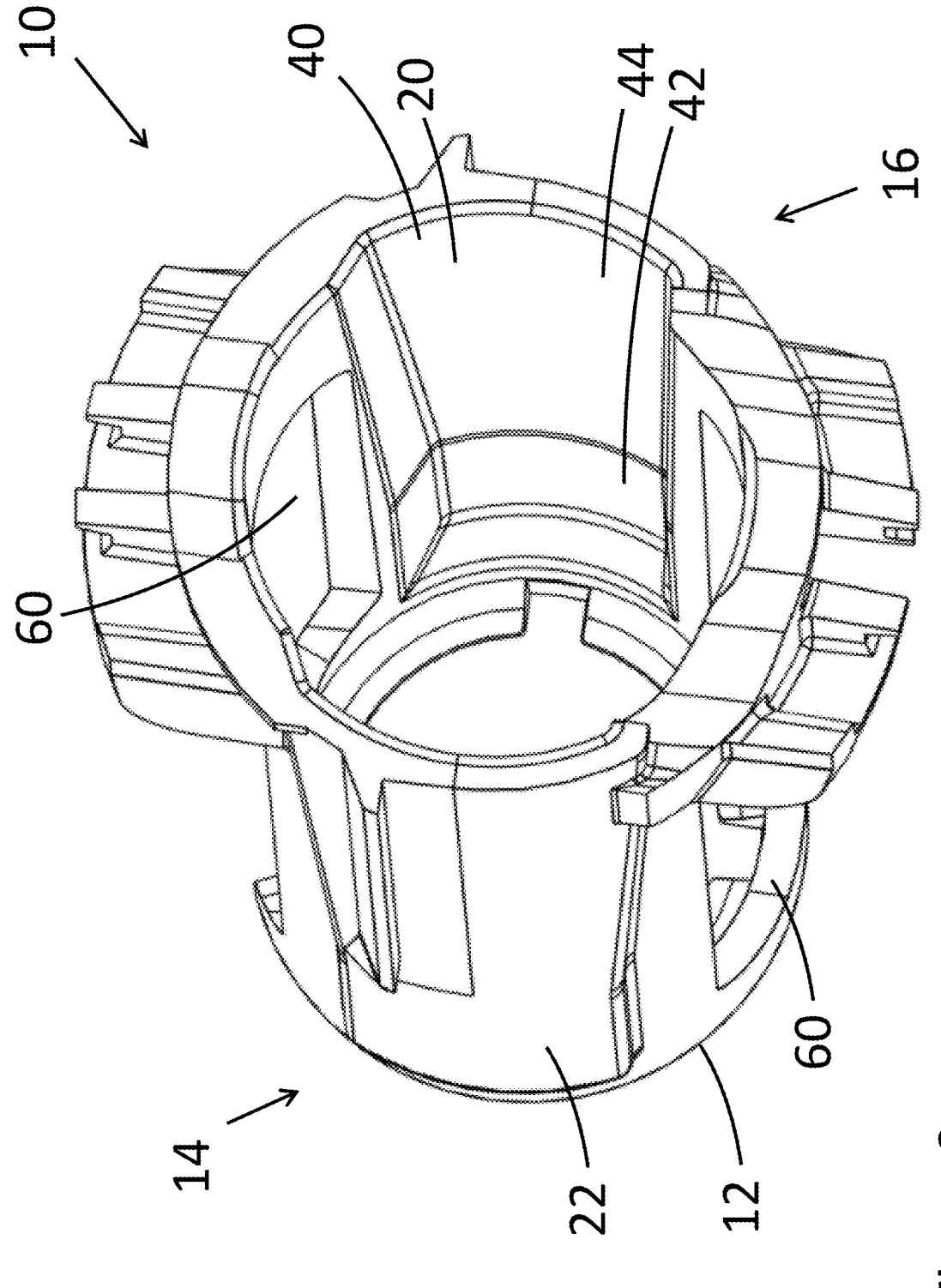
FIG. 2 shows a different perspective view of the syringe holder of FIG. 1.
Figures 3, 4:
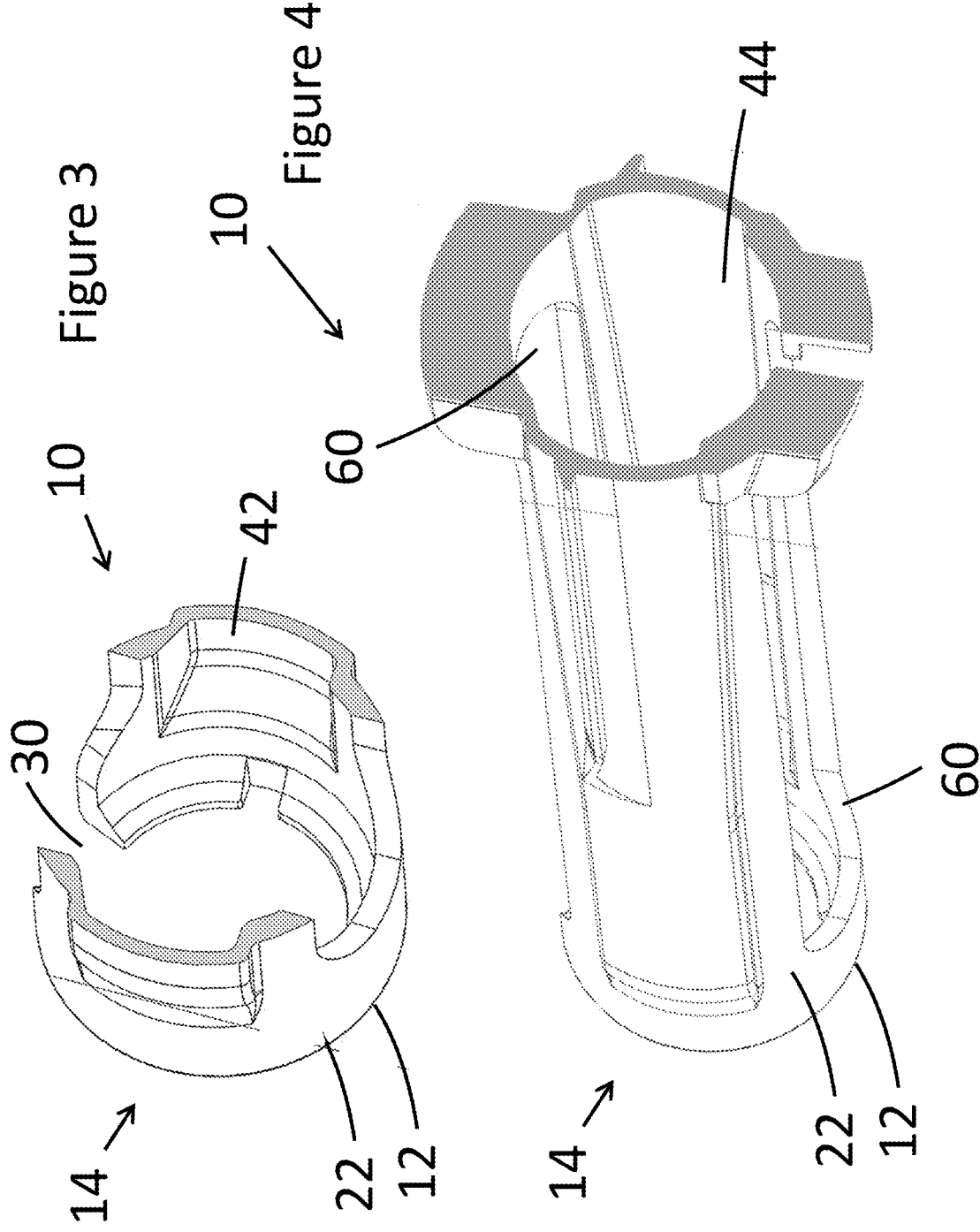
FIG. 3 shows a cross-sectional perspective view of a proximal part of the syringe holder of FIG. 1.
FIG. 4 shows a cross-sectional perspective view of most of the syringe holder of FIG. 1.

FIGS. 1 to 4 show a syringe holder 10 for an autoinjector. The syringe holder 10 comprises a tubular body 12 extending in an axial direction relative to an axis 18 from a proximal end 14 to a distal end 16, and in a circumferential direction 19 around the axis 18. In order to help with reducing stress on the syringe holder, for example, a number of possible syringe holder structures are envisioned. In one example, the tubular body 12 comprises a cut-out extending from the distal end of the tubular body and a flexible expansion joint 70 extending across the cut-out in the circumferential direction. In another example, the tubular body 12 comprises an inner surface 20, an outer surface 22 and a first cut-out 30, the first cut-out 30 extending in the axial direction from the proximal end 14 of the tubular body 12; and either a recess 40 in the inner surface 20 of the tubular body 12, the recess 40 extending in the axial direction from the distal end 16 of the tubular body, or a second cut-out 50 in the tubular body 12, the second cut-out 50 extending in the axial direction from the distal end 16 of the tubular body 12.

The example in FIGS. 1 to 4 will now be described in more detail. In this particular example, two windows 60 are provided, and are arranged opposite one another relative to the axis 18. Two recesses 40 are also provided, and are arranged opposite each other relative to the axis 18 (a recess 40 can be seen directly in FIG. 2, for example; in some Figures such as FIG. 1, where the recess is not directly visible, the structure that forms the recess is marked with reference numeral 40 but with a dotted line). The windows and the recesses overlap each other in the axial direction and are spaced apart in the circumferential direction 19 (although they could alternatively be adjacent to one another or even overlapping in the circumferential direction). In other words, when going in the circumferential direction around the tubular body, there is a first window, then a first recess, then a second window, then a second recess, and then the first window again.

A cut-out 30 extending in the axial direction from the proximal end 14 of the tubular body is also provided. The distal end of the cut-out 30 is adjacent to the proximal end of the second of the two windows in this example. In this example, the proximal end of the tubular body therefore extends around the axis with the exception of the first cut-out 30. The provision of a cut-out 30 makes the shape of the proximal end of the tubular body 12 into a feature that can be described as a C-clip. This can support a syringe in the syringe holder by supporting the proximal end of the syringe within the C-clip.

In this example, two recesses 40 are provided, with the two recesses being the same as one another. The particular structure of the recesses in this example can be seen in FIGS. 2 to 4 in particular. The recesses 40 are deeper at the proximal end than the distal end. The recesses 40 are also narrower in the circumferential direction at the proximal end than at the distal end. The recesses can be thought of as two parts, a proximal portion 42 and a distal portion 44. The surface of the distal portion 44 slopes in the axial direction relative to the axis, and the distal portion 44 of the recess is therefore deeper at the proximal end of the distal portion than at the distal end of the distal portion. The width of the distal portion 44 in the circumferential direction also reduces in the axial direction, with the distal portion 44 being wider in the circumferential direction at the distal end of the distal portion than at the proximal end of the distal portion. Practically speaking, being wider at the distal end of the distal portion can make it easier to align a bypass of a syringe with the recess. Being deeper at the proximal portion can give space for the bypass of the syringe once the syringe is fully inserted in the syringe holder, and can also make it harder for the syringe to simply fall out, due to the shallower parts of the recess at the distal end. This will be described in more detail below.

In this example, the syringe holder extends fully around the axis at the distal end apart from a third cut-out in which an expansion joint 70 is provided. The expansion joint is provided at the distal end of the first of the two windows. The expansion joint is flexible, and deformation of the expansion joint can allow the diameter of the distal end to increase when a syringe is being added into the syringe holder. It can also help remove (eject or de-mould) the component during injection moulding, as the flexibility of the expansion joint allows for easier removal of syringe holders with an under-cut from the core pin, for example an under-cut (overhang) due to a recess that is deeper at the proximal end. In this particular example, the expansion joint is V-shaped, but other shapes are also possible. In general, the expansion joint is optional, as outlined in more detail below.

One of the windows 60 extends from the first cut-out 30 (and can be considered to be a part of the cut-out), although the window could also be spaced apart from the first cut-out in the axial direction. The other window is adjacent to the expansion joint in the longitudinal direction. Although this window could alternatively be spaced apart from the expansion joint, placing the window adjacent to the expansion joint in the axial direction can make it easier for the syringe holder to flex to accommodate a syringe. In other words, the third cut-out extends from the distal end and the expansion joint is in the third cut-out, with the window being an optional extension of the third cut-out.

Instead of an expansion joint, a cut-out (a distal end cut-out) at the position of the expansion joint could instead be provided (without an expansion joint in the cut-out). This would also allow for expansion of the diameter of the distal end of the syringe holder as a syringe is pushed into the syringe holder. In some cases an expansion joint would be preferable, for example to provide structural integrity for the syringe holder, for example. In some cases, however, a distal end cut-out would be preferable; for example, just providing a cut-out could simplify syringe holder manufacture.

When a syringe with a bypass or bypasses is being inserted into a syringe holder as described herein, the proximal end of the syringe (typically including a medicament delivery member such as a needle) is inserted into the distal end of the syringe holder. In the example in FIG. 1, the bypasses are aligned with the recesses. As the bypasses enter the recesses, the recesses can move apart from one another slightly to accommodate the bypasses, because the expansion joint is flexible. In this example, the recesses are deeper at the proximal end of the recesses than at the distal end of the recesses, so once the bypasses reach the proximal end they have more space and no longer need to deform the syringe holder, which can return to its original untensioned state.

In the example in FIG. 1, the recess depth is greater at the proximal end of the recess than at the distal end of the recess, with a sloped recess surface (inner surface of the tubular body), which means that there is more space towards the proximal end to accommodate the bypass or bypasses. As a result, as the syringe is pushed deeper into the syringe holder, there is less and less need for the syringe holder to flex to accommodate the bypass.

In addition to the expansion joint (or alternatively to the expansion joint, in examples without expansion joints), the rest of the tubular body can also flex, and several design features of the syringe holders described herein assist with this flexibility. For example, the proximal end can flex and increase its diameter slightly due to the proximal end cut-out 30 (or cut-outs, in examples such as FIG. 5). The provision of windows 60 can also allow for flexing, particularly of the central portion of syringe holder. Finally, there is a certain amount of flex available within the structure even at points where there is no cut-out or window (with the structure of the syringe holder becoming slightly oval to accommodate the bypass or bypasses), although this can be a source of considerable stress for the syringe holder and this deformation, whilst still possible, is typically minimised or avoided completely by the structure of the example syringe holders described herein. The examples herein have windows, cut-outs and/or recesses for most or all of their length in the axial direction, with examples such as those in FIGS. 1, 5 and 14 having windows, cut-outs and/or recesses for the entirety of their length in the axial direction—this combination helps with reducing stresses during insertion of a syringe with a bypass or bypasses.

Figures 5, 6:
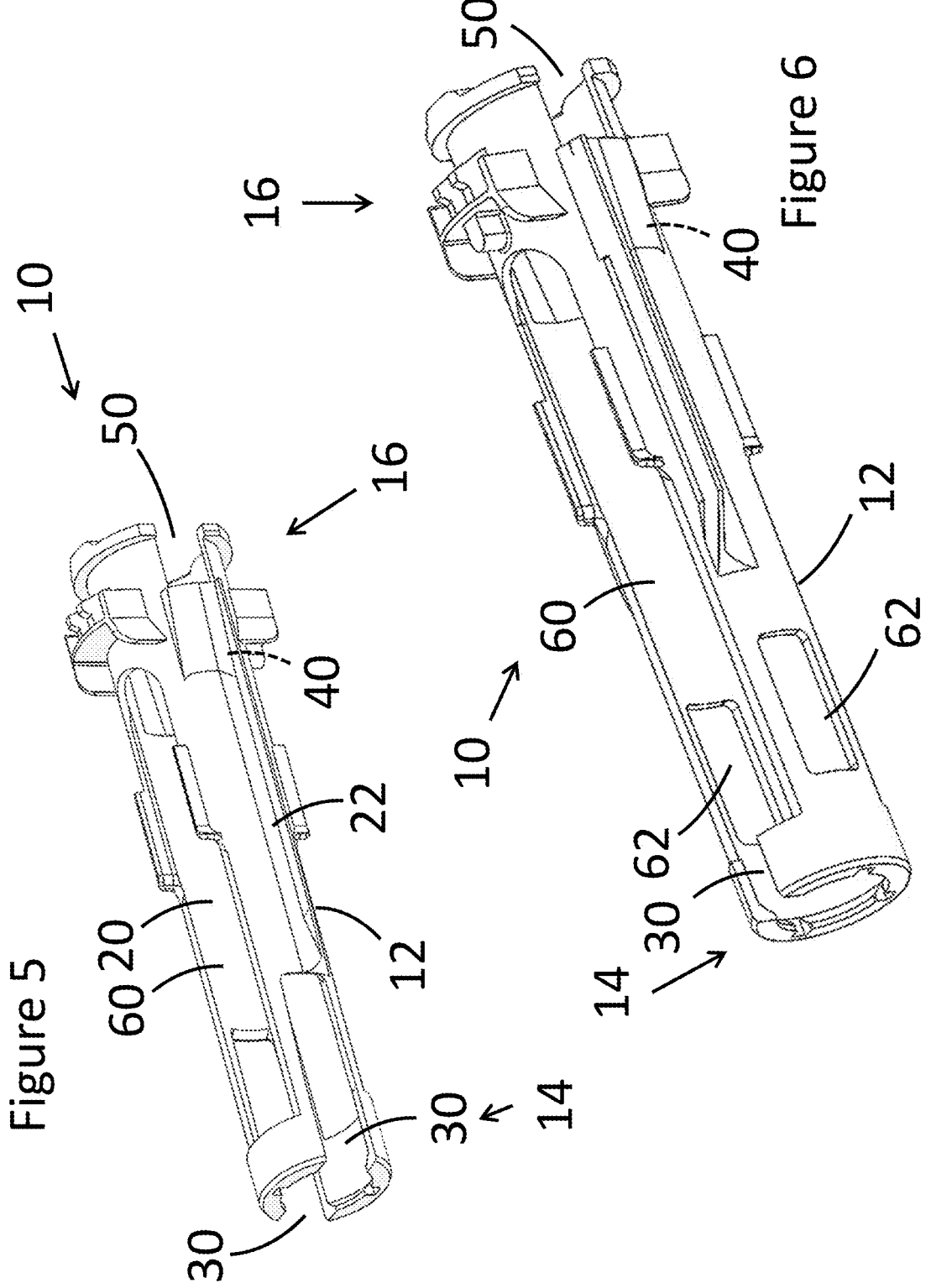
FIG. 5 shows a perspective view of another example syringe holder.
FIG. 6 shows a perspective view of another example syringe holder.

FIG. 5 shows another example syringe holder. Two proximal end cut-outs extend from the proximal end in the axial direction. Two distal end cut-outs extend from the distal end in the axial direction. At the proximal end of each of the two distal end cut-outs, a recess 40 extends in the axial direction. These recesses 40 can be considered as entry chamfers, with the recess being sloped and the distal end of the recess being deeper than the proximal end of the recess. The proximal end cut-outs are aligned in the axial direction with the distal end cut-outs (that is, they overlap in the circumferential direction). Two windows are also provided; the windows are spaced apart from the cut-outs in the circumferential direction (although in examples where the cut-outs do not overlap in the axial direction, the windows can be adjacent to or overlap with the cut-outs in the circumferential direction). When a syringe with two bypasses is placed in the syringe holder, the bypasses would extend in the proximal end cut-outs. In general, provision of a cut-out (or a recess as in FIG. 1) to accommodate a bypass after a syringe with a bypass has been inserted into the syringe holder is beneficial, as it can reduce or avoid ongoing distortion of the syringe holder by the bypass during subsequent transport and storage. Having two proximal end cut-outs means that the syringe holder has 180-degree rotational symmetry, which can make orientation during assembly easier.

Figures 7, 8:
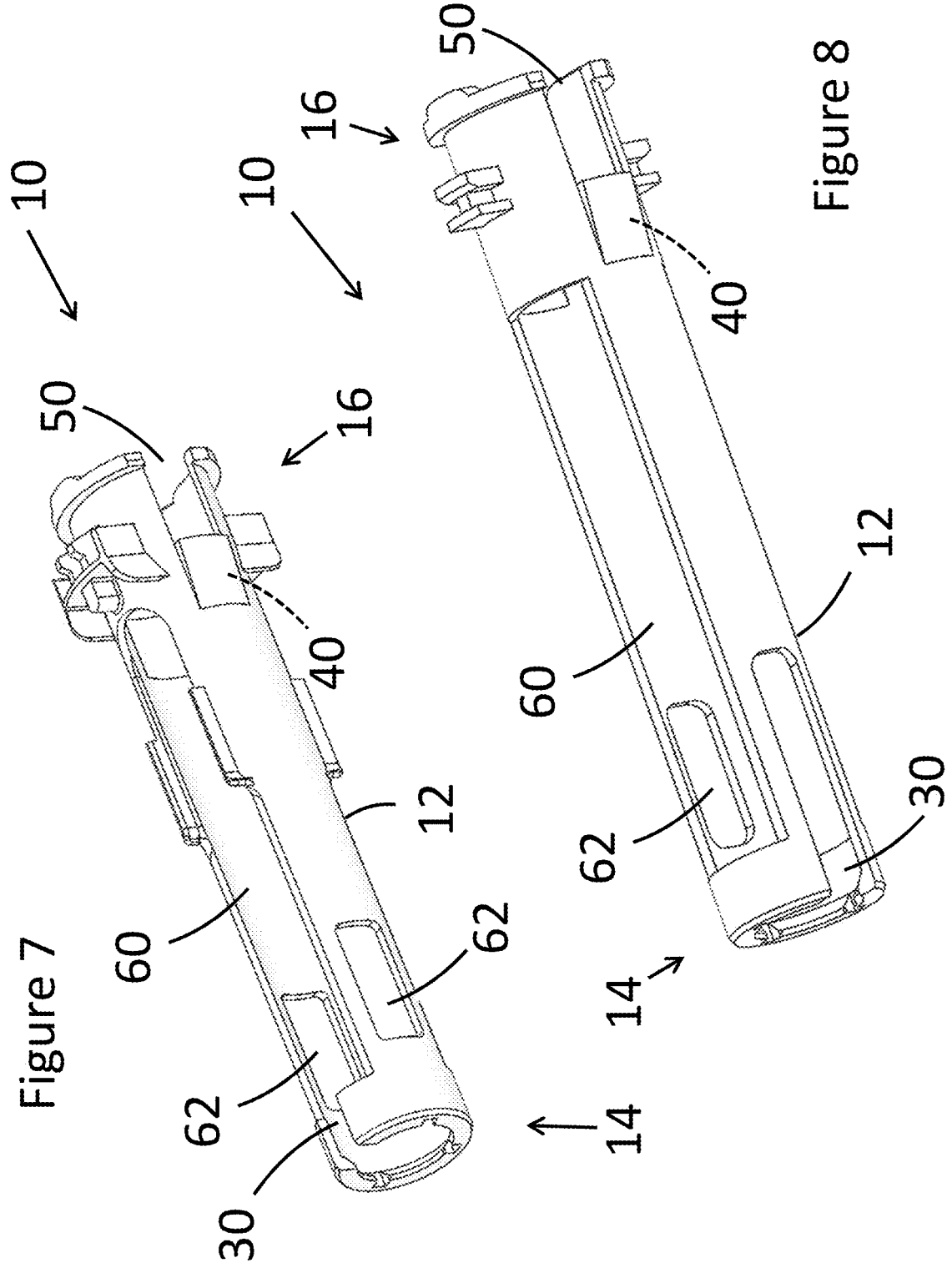
FIG. 7 shows a perspective view of another example syringe holder.
FIG. 8 shows a perspective view of another example syringe holder.
Figure 11:
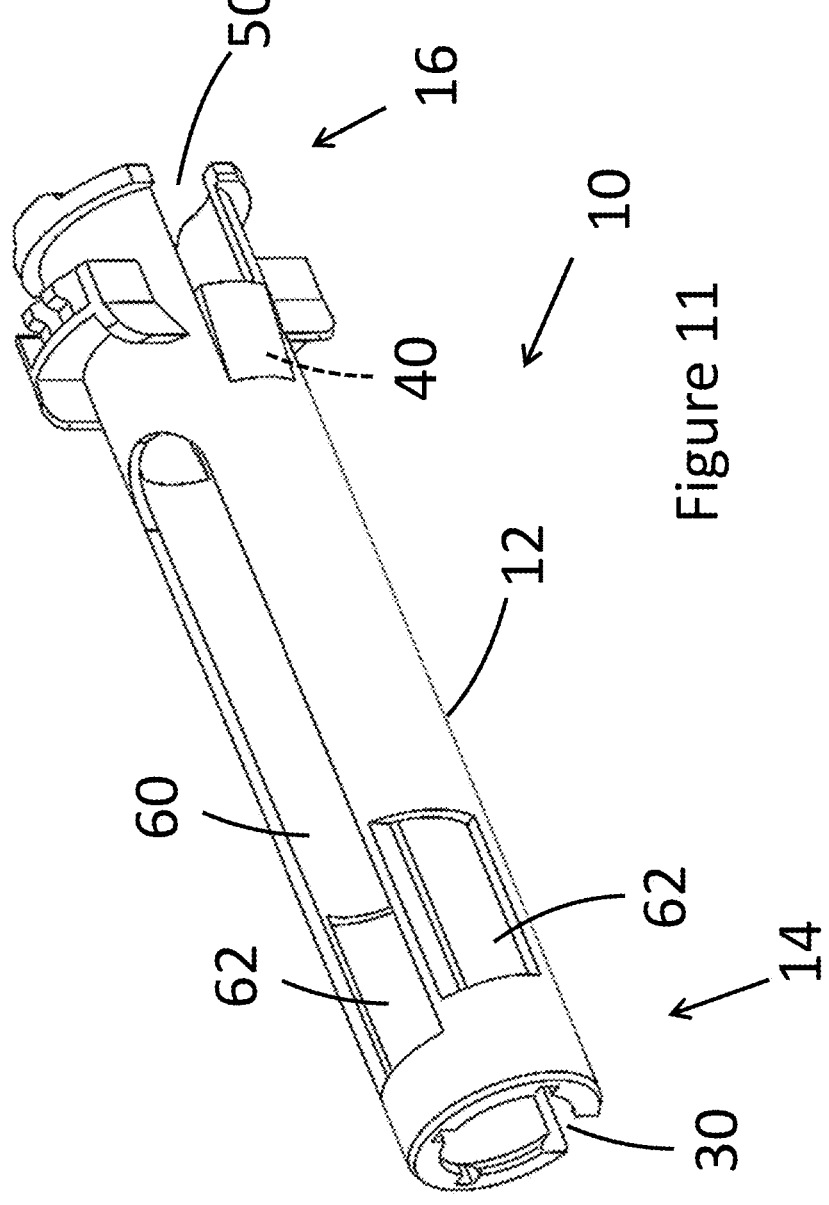
FIG. 11 shows a perspective view of another example syringe holder.

FIG. 6 shows another example syringe holder. Instead of having two proximal end cut-outs extending from the proximal end 14 as in the example in FIG. 5, two windows 62 spaced apart from the proximal end 14 are instead provided, and a single proximal end cut-out is provided at the proximal end (providing a C-clip structure at the proximal end of the tubular body). The structure at the distal end is the same as described for FIG. 5. When a syringe with two bypasses is placed in the syringe holder, the bypasses would extend in the cut-outs that are spaced apart from the proximal end. FIG. 7 shows another syringe holder that is very similar to the example in FIG. 6, as does FIG. 11. There are feature differences between FIGS. 6, 7 and 11, but as these are not core features of the present disclosure currently being described, they will not be described in detail.

FIG. 8 shows another example syringe holder. The design of the syringe holder in FIG. 8 is an intermediate design in between the designs shown in FIG. 5 and the designs shown in FIGS. 6 and 7. The design can basically be described as being the same as that in FIGS. 6 and 7, but with the proximal end cut-out rotated 90 degrees in the circumferential direction so that one of the windows 62 is aligned in the axial direction with the proximal end cut-out (rather than being aligned in the axial direction with the window 60).

Figures 9, 10:
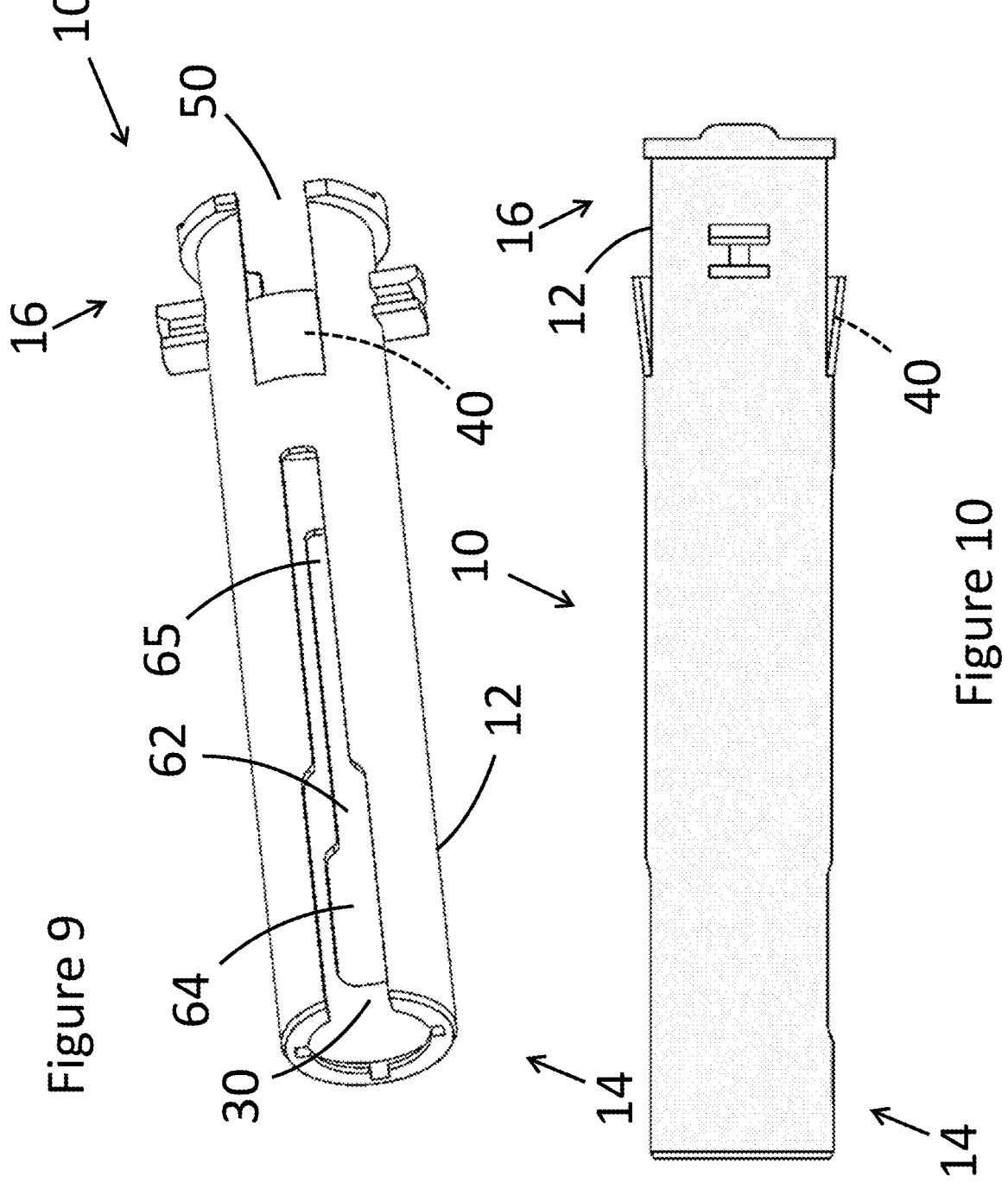
FIG. 9 shows a perspective view of another example syringe holder.
FIG. 10 shows a side view of the syringe holder of FIG. 9.

FIGS. 9 and 10 show another example syringe holder. The design at the distal end is the same as described in previous Figures such as FIG. 5. The syringe holder has a single proximal end cut-out 30. There are two windows 60, with one window aligned in the axial direction with the proximal end cut-out 30 and the other window on the other side of the axis relative to the proximal end cut-out 30. The distal end cut-outs are aligned in the axial direction with the windows 62. The two windows 62 have a proximal portion 64 and a distal portion 65, with the proximal portion being wider in the circumferential direction than the distal portion. When a syringe is placed in the syringe holder, the bypasses would be inside the proximal portion 64 of the window 62. The thinner distal portion 65 of the window can also partly or entirely receive the bypasses during insertion of the syringe into the syringe holder, which can reduce stress on the syringe holder during insertion of the syringe.

Figures 12, 13:
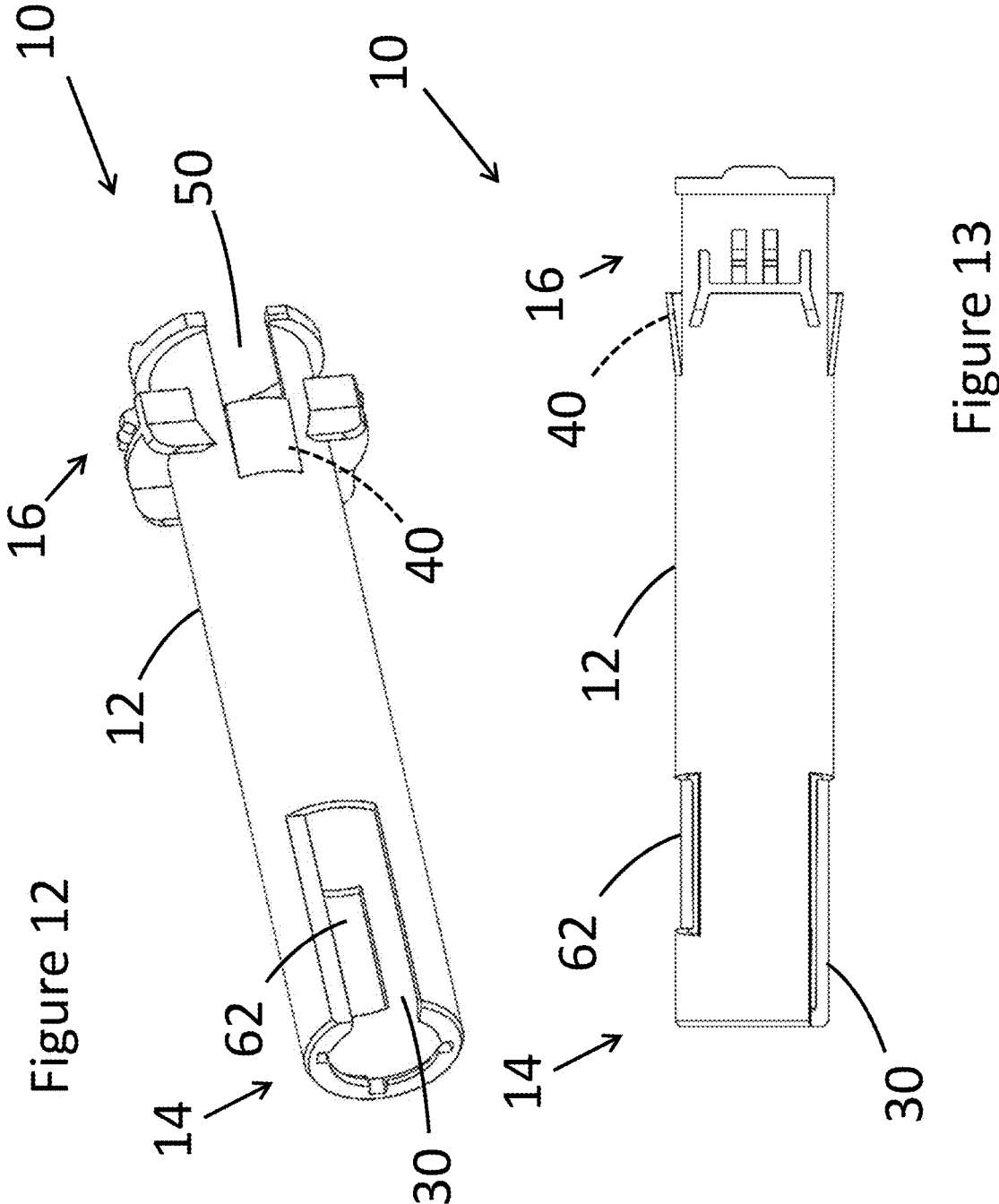
FIG. 12 shows a perspective view of another example syringe holder.
FIG. 13 shows a side view of the syringe holder of FIG. 12.

FIGS. 12 and 13 show another example syringe holder. The design at the distal end is the same as described in previous Figures such as FIG. 5. At the proximal end, a single proximal end cut-out is provided (resulting again in a C-clip design) which is aligned with one of the windows 62. Two windows 62 are provided, with the windows aligned in the axial direction with the distal end cut-outs 50.

The designs in FIGS. 9 and 10 and in FIGS. 12 and 13 do not include windows 60. In general, windows 60 are optional, although they can provide several benefits when provided, including reduction of stress/strain on the syringe holder during syringe insertion and allowing visibility of the drugs within the syringe after the syringe has been placed in the syringe holder. In designs without a window 60 that allows for visibility of the drug, part or all of the syringe holder can be made transparent. This can allow for visibility of the drug despite the lack of a bespoke drug viewing window. Windows 62, which are typically provided to allow space for the bypasses of the syringe once the syringe is placed in the syringe holder, would not necessarily allow clear viewing of the drug due to interference from the bypasses.

Figures 14, 15:
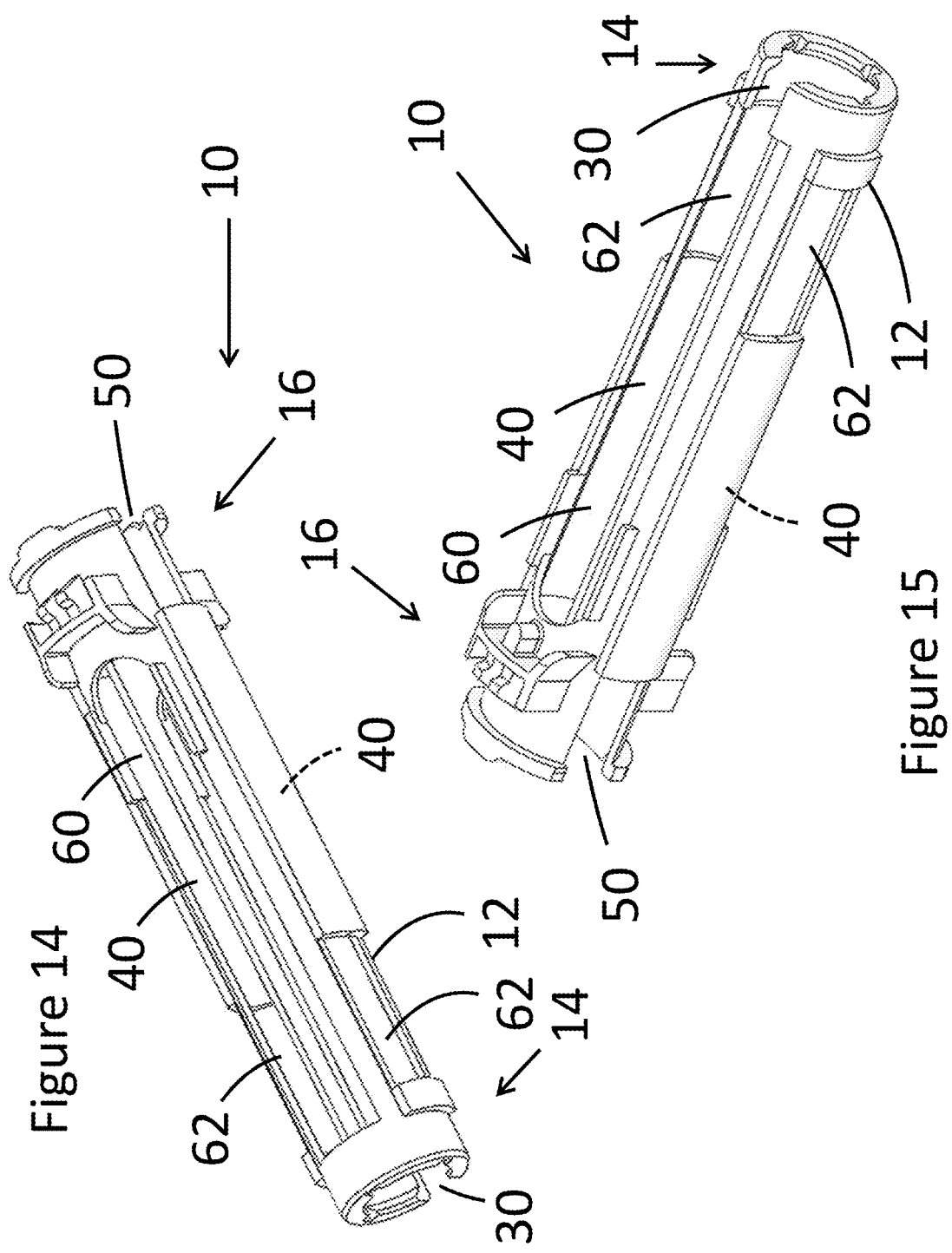
FIG. 14 shows a perspective view of another example syringe holder.
FIG. 15 shows a different perspective view of the syringe holder of FIG. 14.

FIGS. 14 and 15 show another example syringe holder. At the distal end of the tubular body, two distal end cut-outs are provided opposite one another relative to the axis. At the proximal end of each distal end cut-out, a recess extends in the axial direction. At the proximal end of each recess, a window 62 extends in the axial direction. In between the recesses, two windows 60 are provided. At the proximal end of the tubular body, a single proximal end cut-out is provided (i.e. a C-clip design), with the proximal end cut-out aligned with one of the windows 60 in the axial direction.

Figures 16, 17:
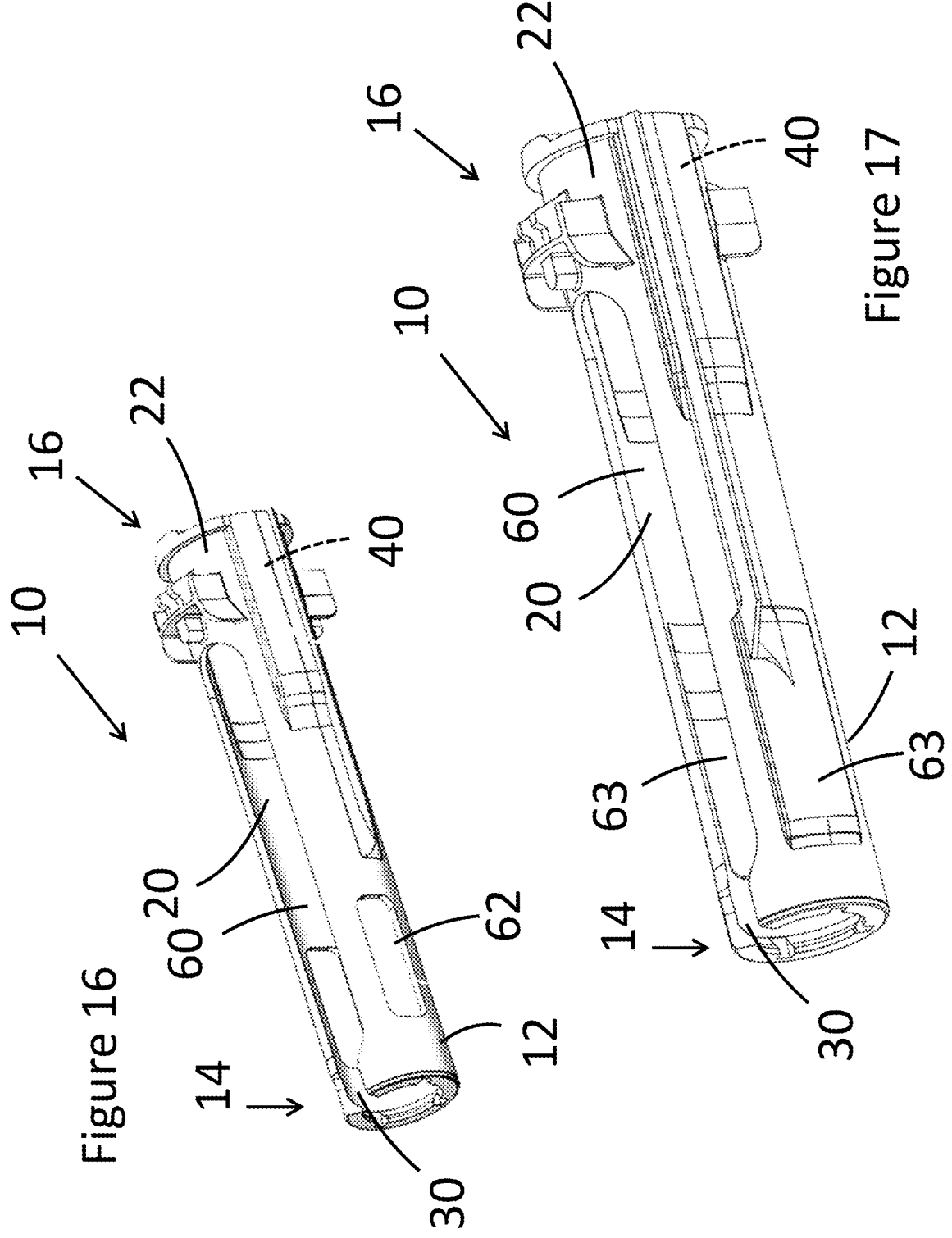
FIG. 16 shows a perspective view of another example syringe holder.
FIG. 17 shows a perspective view of another example syringe holder.

FIG. 16 shows another example syringe holder, with elements of the examples in FIGS. 1 and 6 in particular. Two recesses 40 extend from the distal end of the tubular body 12. There are no distal end cut-outs. The proximal end has a C-clip; that is, a proximal end cut-out 30. A window 60 extends from the distal end of the proximal end cut-out, and a second window (not visible) is also provided opposite the window relative to the axis. Two windows 62 are also provided. FIG. 17 shows another example syringe holder. This syringe holder is the same as the example in FIG. 16, but instead comprises two bypass recesses 63 instead of the windows 62.

In general, the syringe holder 10 is a syringe holder for a medicament delivery device such as an autoinjector. Although the syringe holders described herein could also be useful for syringes in general, they can be particularly beneficial when the syringe being inserted into the syringe holder is a dual-chamber syringe with at least one bypass (external bypass), as the bypass tends to increase the width of the syringe by protruding out further from its central axis compared to the rest of the syringe. In the context of this application, a syringe is typically a medicament container that can be included within a medicament delivery device such as an autoinjector. The syringe typically includes a medicament delivery member such as a needle, along with a needle shield. A completed autoinjector that includes a syringe holder as described herein would typically include a housing, the syringe holder inside the housing, the syringe (typically dual-chamber with one or more bypasses as mentioned above) and a cap, for example. An example of an autoinjector can be found in WO2011/123024, which is incorporated herein in its entirety by reference.

The syringe could typically have two bypasses at opposite sides of the syringe, or could have one, three or more bypasses spaced around the syringe in the circumferential direction, and the syringe holder could be designed accordingly. As such, although two recesses are shown in the examples, in each case only one recess is required (and the same for windows and cut-outs in the examples). In some examples, two recesses or cut-outs are provided opposite each other relative to the axis even though there is only one bypass, as this can make assembly easier by providing 180-degree symmetry (though some features such as the C-clip do not need 180-degree symmetry), allowing the syringe holder to function in two different orientations even with a single bypass.

The tubular body 12 in the various embodiments herein is shown as a cylindrical body with a circular cross section perpendicular to the axis, but other shapes are also possible. The inner surface 20 is the surface of the tubular body facing generally towards the axis, and the outer surface 22 is the surface of the tubular body facing generally away from the axis.

The cut-out 30 (proximal end cut-out) is shown on the opposite side of the axis relative to the expansion joint 70 in FIG. 1, but could be at a different location, for example on the same side (overlapping in the circumferential direction) or 90 degrees removed in the circumferential direction (rather than the 180 degrees shown in FIG. 1). Rather than one cut-out 30, two or more cut-outs could be provided. With one proximal end cut-out, the proximal end of the syringe holder can be thought of as a C-clip. Alternatively, some examples can include no proximal end cut-outs 30.

Similarly, where recesses 40 are provided, the examples herein shown two recesses. However, one, three or more recesses could alternatively be provided, and the examples shown herein could all be modified to only have one recess instead of the two recesses shown. A recess such as the recess in FIG. 1 can be replaced by a cut-out, or combined with a cut-out (as in the examples in FIG. 5 onwards). In general, when a recess is provided, a portion of the inner surface of the tubular body is the surface of the recess. The surface of the recess could be parallel to the axis (e.g. FIG. 15), or partially parallel to the axis (proximal portion 42 in FIG. 2) and partially angled relative to the axis (distal portion 40 in FIG. 2), such as in FIGS. 2, 16 and 17, or angled relative to the axis (FIGS. 4 to 13). Where part or all of the axis is angled relative to the axis, it can be angled so that the surface is angled to face towards the distal end (e.g. FIGS. 5 to 13 and 16 to 17) or angled to face towards the proximal end (e.g. FIG. 2).

A particular shape of recess is shown in FIG. 1, with a proximal portion 42 and a distal portion 44, but other shapes of recess could also be used in the example in FIG. 1, for example a recess shaped as in FIG. 5 or FIG. 14.

Typically, the distal end cut-out 50/recess 40 is aligned with the proximal end cut-out 30/the window 62/the bypass recess 63 for the bypass, which can help with assembly.

As mentioned above, distal end cut-outs 50 can have expansion joints 70 in or can be without expansion joints 70. In general, one or more distal end cut-outs can be provided, with none, some, or all of the distal end cut-outs having expansion joints in.

This description describes various windows (cut-outs). The description distinguishes between windows 60 (which typically provide a window through which the drug could be seen) and windows 62 (which typically provide a space for the bypass of the syringe), though the two can be combined or interchanged and are not necessarily structurally different.

In general, windows 62 can also be replaced with bypass recesses such as those in FIG. 17. In general, there are several different possible functions for windows described herein, including to allow visibility of the drug (e.g. FIG. 1), to allow space for a syringe bypass during or after assembly (e.g. FIG. 9), and to allow or help allow flexing of the syringe holder when the syringe is inserted. Any given window can have one or more functions, depending on the particular design of the syringe holder.

In general, windows 60 are optional and could be removed from the examples herein, although when provided they can also help reduce stress on the syringe holder during assembly, for example by making it easier for the syringe holder to flex to accommodate bypasses. One example of this is in FIG. 5, where the provision of a window or windows 60 can help allow the syringe holder to flex and allow a syringe to pass into the syringe holder.

Various different shapes for windows are possible beyond those shown in the examples, and would depend on the particular device in which the syringe holder is being used and on the shape of the syringe in which the syringe holder is being used. Windows are typically rectangular or oval with the longer side extending in the axial direction, and may have right-angled corners (e.g. window 60 in FIG. 8), slightly curved corners (e.g. window 62 in FIG. 8), or broadly curved corners (e.g. distal end of window 60 in FIG. 11). Irregularly shaped windows are also possible, such as window 62 in FIG. 9.

Similarly, the shapes of the cut-outs described herein could be varied, with rectangular shaped cut-outs with right-angled corners, slightly curved corners, broadly curved corners or a mix of corner shapes being possible. Irregularly shaped cut-outs are also an option.

Although an expansion joint 70 is only shown in the example in FIG. 1, an expansion joint could also be provided in the other examples described herein. More than one expansion joint could also be provided; for example, a second expansion joint could be provided opposite the first expansion joint (i.e. on the other side of the axis) in the example shown in FIG. 1.

One possible expansion joint shape is shown in FIG. 1, namely a V-shaped expansion joint. The protrusions extending radially away from the expansion joint are not necessary for the functioning of the expansion joint. Other shapes of expansion joints are possible, for example W-shaped, S-shaped or spring-shaped expansion joints. The expansion joint would typically flex in the circumferential direction, as this allows for the expansion joint to take up a minimum of space in the radial direction, but flexing in the radial direction instead or as well is also an option.

A number of the cut-outs and windows are adjacent to one another, meaning that often a cut-out and its adjacent window effectively provide a single larger cut-out. This is the case, for example, in FIGS. 6, 7, 11 and 15 (cut-out 30 and window 60), and in FIGS. 9 and 12 (cut-out 30 and window 62). It is also effectively the case in FIGS. 5 and 8, for example, where the distal end of the cut-out(s) 30 could be considered to be a window 62.

Where two or more of the same feature are provided (for example cut-outs, recesses or the like), they can be the same (as is mostly the case in the examples herein) or different from one another.

Various other modifications to the embodiments described are possible and will occur to those skilled in the art without departing from the present disclosure which is defined by the following claims.

The invention claimed is:

1. A syringe holder for an autoinjector, the syringe holder comprising:

a tubular body extending around an axis in a circumferential direction and along the axis in an axial direction from a proximal end to a distal end, where the tubular body comprises:

a cut-out extending from the distal end of the tubular body and a flexible expansion joint, wherein the flexible expansion joint extends across the cut-out in the circumferential direction;

an inner surface and an outer surface, and wherein the tubular body comprises a recess in the inner surface; and a second cut-out extending from the distal end of the tubular body, wherein the second cut-out is spaced apart from the cut-out in the circumferential direction, and wherein the proximal end of the second cut-out is adjacent to the distal end of the recess.

2. The syringe holder of claim 1, wherein the tubular body comprises a window, the window extending in the axial direction and spaced apart from the distal end of the tubular body and from the proximal end of the tubular body.

3. The syringe holder of claim 2, wherein the tubular body comprises two windows, each window extending in the axial direction and spaced apart from the distal end of the tubular body and from the proximal end of the tubular body.

4. The syringe holder of claim 3, wherein a first of the two windows extends from the proximal end of the cut-out, and wherein a second of the two windows extends from the distal end of the proximal end cut-out.

5. The syringe holder of claim 1, wherein the tubular body comprises a proximal end cut-out extending from the proximal end of the tubular body.

6. The syringe holder of claim 1, wherein the recess extends from the distal end of the tubular body.

7. The syringe holder of claim 1, wherein the recess is deeper at the proximal end of the recess than at the distal end of the recess.

8. The syringe holder of claim 1, wherein a portion of the inner surface in the recess is angled relative to the axis.

9. The syringe holder of claim 1, wherein the recess is configured to receive a part of a syringe when said syringe is inserted into the syringe holder during assembly of a medicament delivery device.

10. An autoinjector comprising the syringe holder of claim 1.

11. A syringe holder for an autoinjector, the syringe holder comprising a tubular body extending around an axis in a circumferential direction and along the axis in an axial direction from a proximal end to a distal end, wherein the tubular body comprises an inner surface and an outer surface, a first cut-out in the tubular body, the first cut-out extending in the axial direction from the proximal end of the tubular body; and a second cut-out in the tubular body, the second cut-out extending in the axial direction from the distal end of the tubular body, wherein the tubular body comprises a recess that extends from the proximal end of the second cut-out.

12. The syringe holder of claim 11, wherein the recess is deeper in the direction perpendicular to the axis at a distal end of the recess than at a proximal end of the recess.

13. An autoinjector comprising the syringe holder of claim 11.

*    *    *    *    *